US00PP15375P2

(12) United States Plant Patent
Mowrey et al.

(10) Patent No.: US PP15,375 P2
(45) Date of Patent: Nov. 30, 2004

(54) STRAWBERRY PLANT NAMED 'DRISCOLL MARIN'

(50) Latin Name: *Fragaria×ananassa*
Varietal Denomination: Driscoll Marin

(75) Inventors: Bruce D. Mowrey, Watsonville, CA (US); Larry T. Kodama, Freedom, CA (US); JoAnne Coss, Salinas, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 98 days.

(21) Appl. No.: 10/295,644

(22) Filed: Nov. 15, 2002

(51) Int. Cl.[7] ..... A01H 5/00
(52) U.S. Cl. ..... Plt./209
(58) Field of Search ..... Plt./209

*Primary Examiner*—Bruce R. Campell
*Assistant Examiner*—Michelle Kizilkaya
(74) *Attorney, Agent, or Firm*—Jones Day

(57) ABSTRACT

This invention relates to a new and distinct variety of strawberry named 'Driscoll Marin'. The variety is similar to the varieties 'Ana Maria' and 'San Juan'. The variety is distinguished from 'Ana Maria' and 'San Juan', in particular, by its petiole color, achene coloration, growth habit and density, weak vigor, thick stolons, and inflorescence positioned above the foliage.

4 Drawing Sheets

Latin name of the genus and species of the plant claimed: The variety is botanically identified as *Fragaria×ananassa.*

BACKGROUND OF THE INVENTION

The new variety originated as a result of a controlled cross between the strawberry plants '67C253' (unpatented Driscoll variety) and 'Lido' (U.S. Plant Pat. No. PP10,534, issued Aug. 4, 1998) in an ongoing breeding program, and was discovered in a controlled breeding plot, in Monterey County, Calif. in May 1998. The original seedling was asexually propagated by stolons in a nursery in Shasta County, Calif. Propagules were transplanted to a controlled breeding plot in Ventura, County, Calif. where it was identified and selected for further evaluation. 'Driscoll Marin' was subsequently asexually propagated and underwent further testing at various locations in Monterey county, Calif. for two years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Driscoll Marin'. The variety is botanically identified as *Fragaria×ananassa*. The new variety is distinguished from other varieties by a number of characteristics as set forth in Tables 1 and 2.

COMPARISON TO SIMILAR VARIETIES

The varieties which we believe to be similar to 'Driscoll Marin' from those known to use are 'Ana Maria' (U.S. Plant Pat. No. PP11,035, issued Aug. 17, 1999) and 'San Juan' (U.S. Plant Pat. No. PP12,899, issued Sep. 3, 2002). There are several characteristics of the new variety that are different from, or not possessed by 'Ana Maria', and 'San Juan'. The new variety has achene coloration that is greyed purple to yellow, weak interveinal blistering on leaves, and a revolute terminal leaflet margin.

'Driscoll Marin' differs from its parent '67C253' (unpatented Driscoll variety) in several characteristics, including, but not limited to, being adapted to Northern California climate, where '67C253' is adapted to a Southern California climate. 'Driscoll Marin' also exhibits superior fruit firmness in comparison to '67C253'. 'Driscoll Marin' differs from its patent 'Lido' (U.S. Plant Pat. No. PP10,534) in several characteristics, including, but not limited to, exhibiting intense red fruit flesh in comparison to the pale pink fruit flesh color of 'Lido'. 'Driscoll Marin' also has superior late season production in comparison to 'Lido'.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics. The plants of 'Driscoll Marin' characterized in the botanical descriptions and depicted in the figures were grown outdoors in an annual production system. Measurements were taken during the late summer in the second half of the production season.

DESCRIPTION OF THE NEW VARIETY

Figure 1:
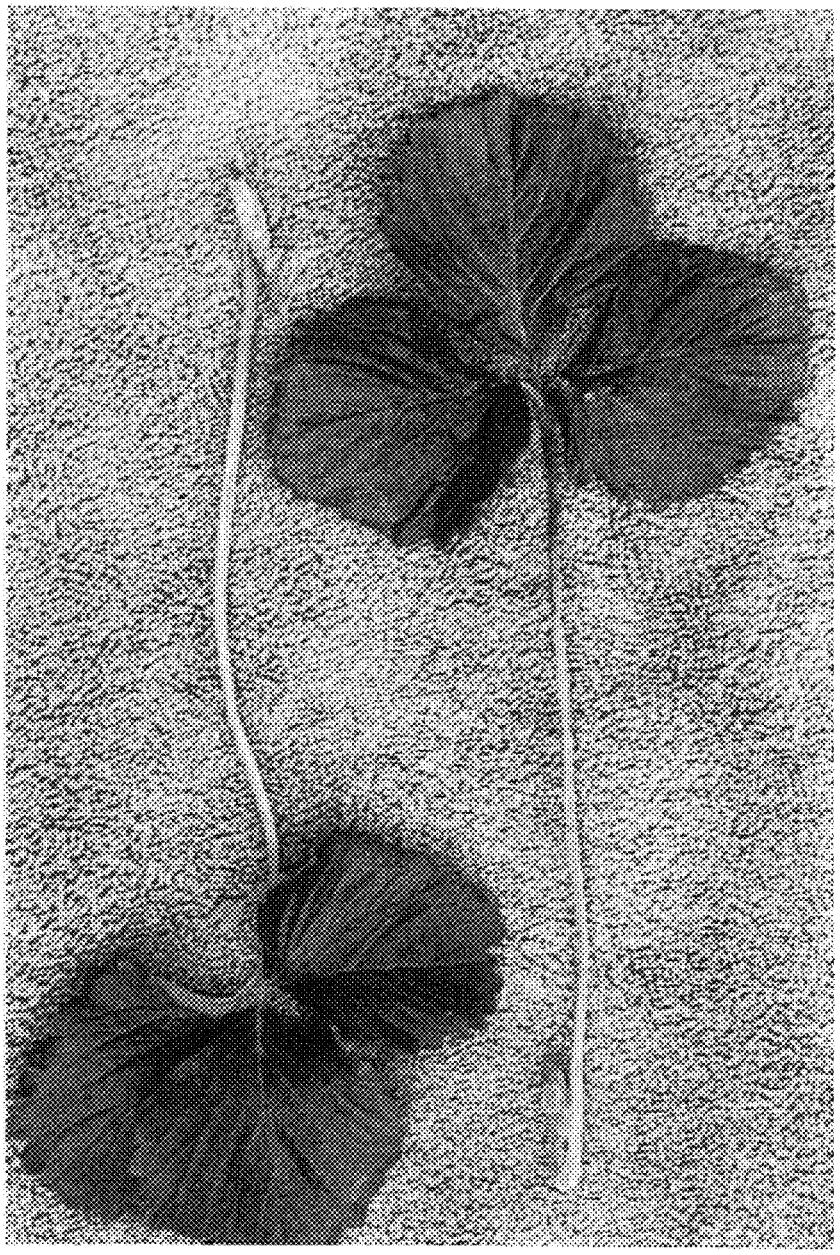
FIG. 1 shows leaves of the plants with three leaflets.
Figure 2:
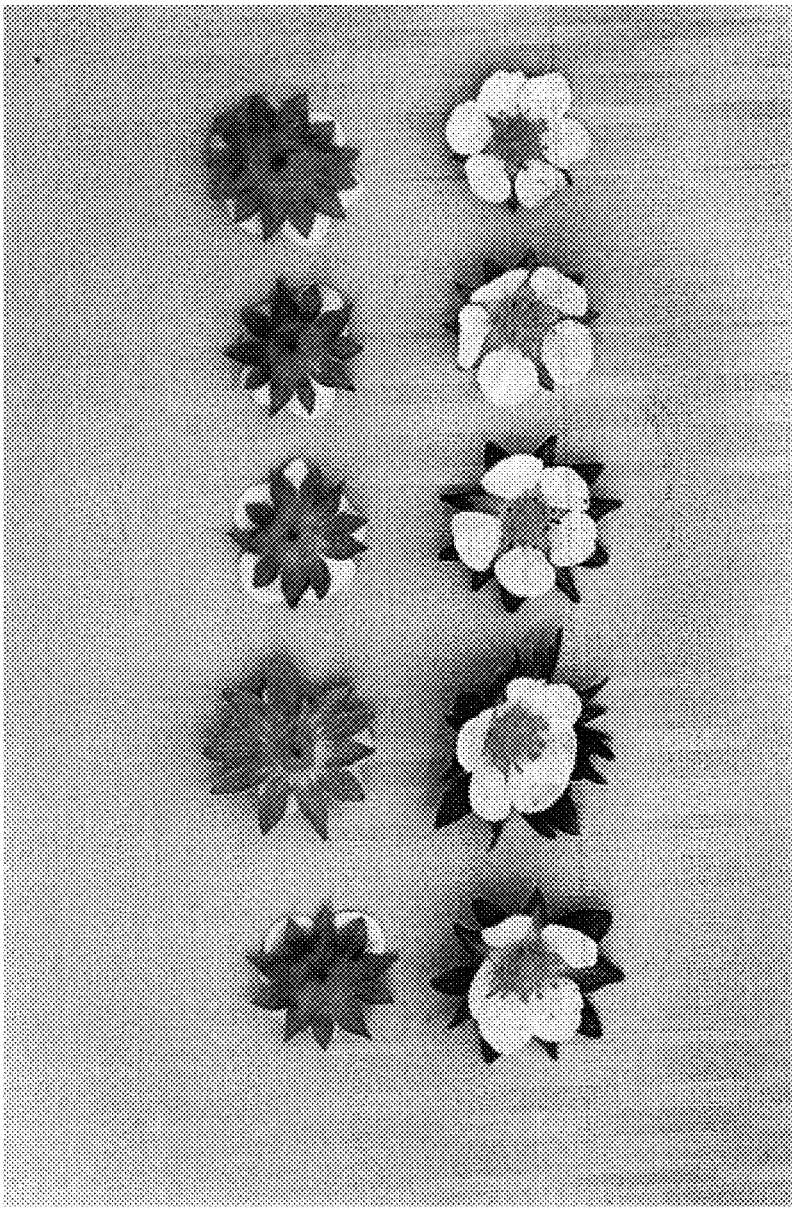
FIG. 2 shows the upper side and under side of the flowers.
Figure 3:
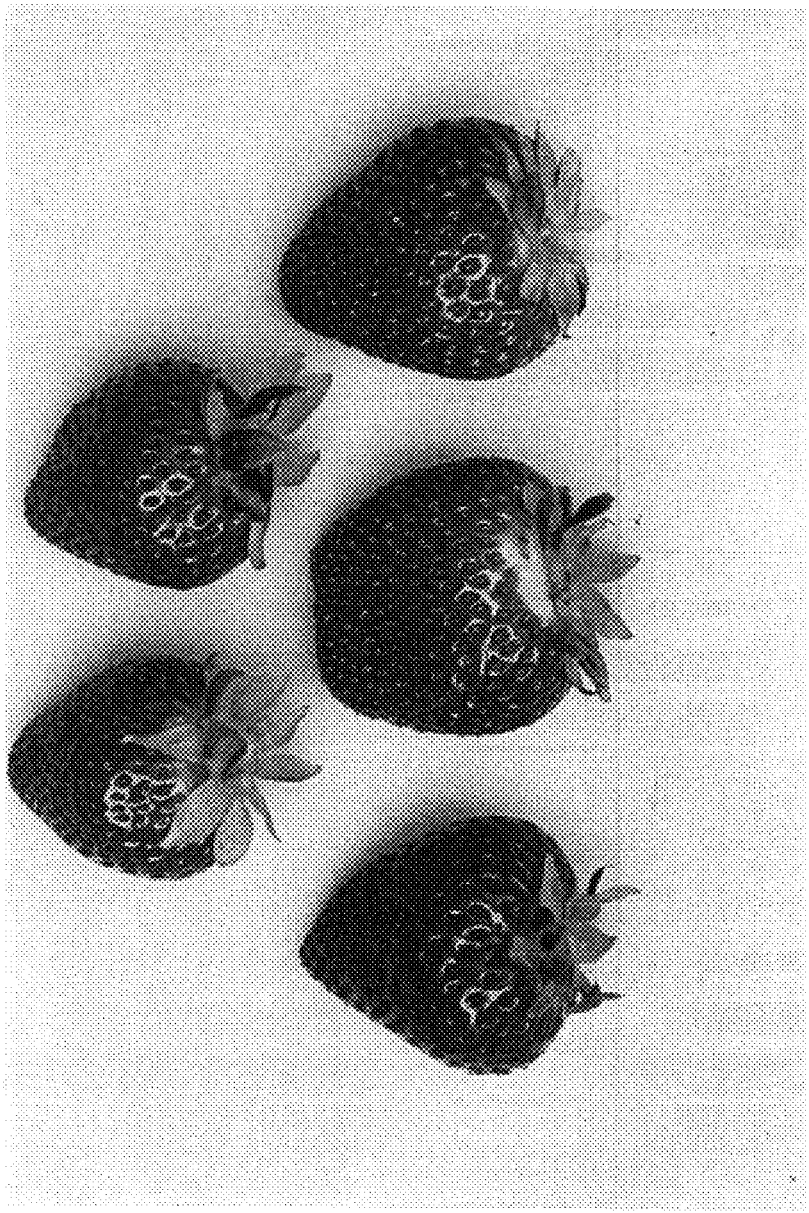
FIG. 3 shows a close-up of the strawberry.
Figure 4:
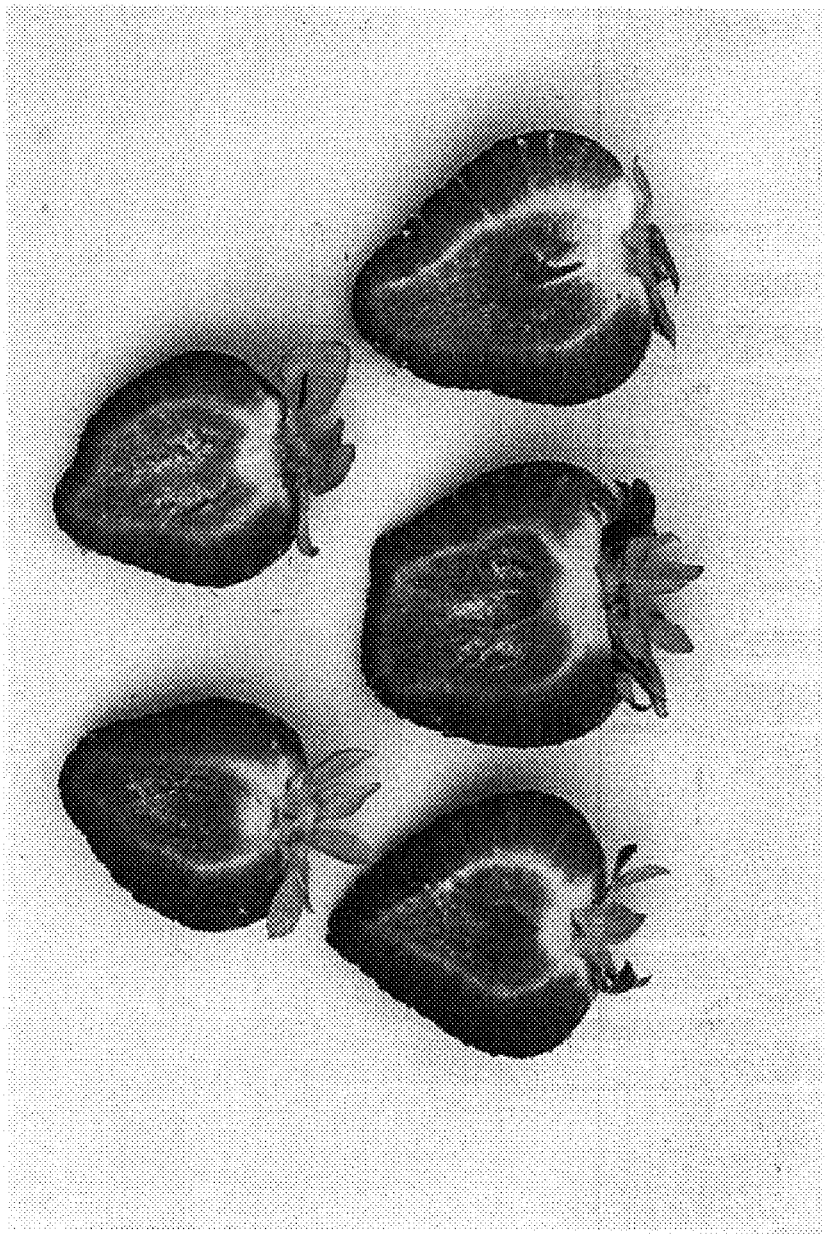
FIG. 4 shows the strawberry in longitudinal cross-section

The following detailed description of the new variety is based upon observations taken of plants and fruit grown in Monterey county, Calif., U.S.A. Observations of 'Driscoll Marin', 'Ana Maria' and 'San Juan' were taken in side by side comparison in 2002. This description is in accordance with UPOV terminology. Color designations, color descriptions, and other phenotypical descriptions may deviate from the stated values and description depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2, 3 and 4. In the tables, the flowers described are secondary flowers except where indicated. The fruit described in the secondary fruit on one year old plants. Fruit and flower measurements are an average of both primary and secondary fruit and flowers. In particular, the reproductive structures of 'Driscoll Marin' are fully self-fertile and typical of the species. Anther color is yellow, 13A, pistil color is yellow, 13A, and receptacle color is 150G, yellow green.

Table 1 provides information on the plant and fruit characteristics of the new variety 'Driscoll Marin' compared with characteristics of 'Ana Maria' and 'San Juan'. Table 2 provides additional information of the plant and fruit characteristics of the new variety 'Driscoll Marin' compared with characteristics of the varieties 'Ana Maria' and 'San Juan'. Table 3 provides reactions of the new variety to stresses, pests, and diseases as compared to the varieties 'Ana Maria' and 'San Juan'. Table 4 provides isozyme characteristics of the new variety as compared to the varieties 'Ana Maria' and 'San Juan'.

TABLE 1

QUANTITATIVE COMPARISON OF 'DRISCOLL MARIN', 'ANA MARIA', AND 'SAN JUAN'

| | 'Driscoll Marin' | 'Ana Maria' | 'San Juan' |
|---|---|---|---|
| Plant Characteristics | | | |
| Height of Plant (cm) | 28.8 | 33.6 | 30.1 |
| Spread of Plant (cm) | 43.5 | 51.8 | 47.1 |
| Number of Crowns | 4.1 | 4.3 | 3.8 |
| Leaf Characteristics | | | |
| Terminal Leaflet Length (cm) | 8.0 | 9.8 | 8.3 |
| Terminal Leaflet Width (cm) | 7.8 | 9.5 | 7.9 |
| Terminal Leaflet Length/Width Ratio | 1.03 | 1.03 | 1.05 |
| # Teeth/Terminal Leaflet | 20.3 | 21.3 | 24.6 |
| Color of upper side | medium to dark green 147A | medium green 147A | medium to dark green 147A |
| Color of under side | light green 147B | light green 148B | light green 147C |
| Petiole Length (cm) | 18.1 | 20.7 | 19 |
| Petiole Color | 145A | 145B | 149A |
| Bract Frequency | 58% typically paired | 67% typically single | 25% typically paired |
| Stipule Length (cm) | 3.6 | 3.4 | 3.6 |
| Stipule Width (cm) | 1.10 | 1.07 | 1.11 |
| Flower Characteristics | | | |
| Petal Length (cm) | 1.16 | 1.29 | 1.05 |
| Petal Width (cm) | 1.09 | 1.22 | 1.10 |
| Petal Length/Width Ratio | 1.07 | 1.05 | 0.95 |
| Flower Diameter (cm) | 2.15 | 2.15 | 2.15 |
| Calyx Diameter (cm) | 2.85 | 3.07 | 2.91 |
| Fruiting Truss Length (cm) | 31.1 | 36.9 | 34.0 |

TABLE 1-continued

QUANTITATIVE COMPARISON OF 'DRISCOLL MARIN', 'ANA MARIA', AND 'SAN JUAN'

| | 'Driscoll Marin' | 'Ana Maria' | 'San Juan' |
|---|---|---|---|
| Petal Color (cm) | 155D | 155D | 155C |
| Fruit Characteristics | | | |
| Fruit Length (cm) | 4.26 | 3.99 | 4.33 |
| Fruit Width (cm) | 3.52 | 3.74 | 3.85 |
| Fruit Length/Width Ratio | 1.21 | 1.07 | 1.13 |
| Average Berry Weight (g) | 24.3 | 22.5 | 28.4 |
| External Color | dark red 53A | red 46A | dark red 53A |
| Internal Color | red 45A | orange red 44B | red 44A |
| Average % brix | 8.12 | 8.34 | 8.97 |
| Brix/Acid Ratio | 11.36 | 13.48 | 15.07 |
| Achene Coloration | greyed purple to yellow 187B to 16A | dark red to yellow 46B to 16A | dark red to yellow 46B to 16A |
| Yield (g/plant) | 1,349 | 1,504 | 1,225 |

TABLE 2

QUALITATIVE COMPARISON OF 'DRISCOLL MARIN', 'ANA MARIA' AND 'SAN JUAN'

| | 'Driscoll Marin' | 'Ana Maria' | 'San Juan' |
|---|---|---|---|
| Plant | | | |
| Habit | flat | globose to upright | globose to flat globose |
| Density | open | medium to open | medium |
| Vigor | weak | strong | medium |
| Leaf | | | |
| Shape in cross section | slightly concave | slightly concave to flat | flat to slightly convex |
| Interveinal blistering | weak | medium to strong | medium to strong |
| Glossiness | weak | medium | weak to medium |
| Number of leaflets | three only | three only | weak sometimes more than 3 leaflets (approx. 17% of leaves) |
| Terminal leaflet margin profile | revolute | flat | revolute to flat |
| Terminal leaflet shape of base | obtuse | rounded to oblique | obtuse to rounded |
| Terminal leaflet shape of teeth | obtuse | obtuse | rounded |
| Stipule pubescence | medium | sparse | medium |
| Petiole pubescence | medium | sparse | medium |
| Petiole pose of hairs | outward to downward | outward | outward to downward |
| Stolon | | | |
| Amount | medium to many | medium to many | medium to many |
| Anthocyanin coloration | medium | medium | strong |
| Thickness | thick | thin to medium | medium |
| Pubescence | medium | sparse to medium | medium |

TABLE 2-continued

QUALITATIVE COMPARISON OF 'DRISCOLL MARIN', 'ANA MARIA' AND 'SAN JUAN'

| | 'Driscoll Marin' | 'Ana Maria' | 'San Juan' |
|---|---|---|---|
| Inflorescence | | | |
| Position relative to foliage | above | level to above | beneath to level with |
| Diameter of calyx relative to corolla on secondary flowers | same size to larger | smaller to same size | larger |
| Diameter of inner calyx relative to outer on secondary flowers | same size | smaller to same size | same size |
| Spacing of petals | free to touching | free to touching | overlapping |
| Fruiting Truss | | | |
| Attitude at first picking | prostrate | semi-erect | prostrate |
| Fruit | | | |
| Predominant shape | conical to almost cylindrical | conical | conical to almost cylindrical |
| Difference in shapes between primary and secondary fruits | marked with primaries being flattened and secondary fruit more conical | none to very slight | moderate |
| Band without achenes | very narrow to narrow | narrow to medium | narrow |
| Unevenness of surface | medium | weak | medium |
| Evenness of color uneven | even | even | even |
| Glossiness | strong | strong | very strong |
| Insertion of achenes | level with surface | level with surface | level with surface |
| Insertion of calyx | level | level with to set above | level |
| Pose of the calyx segments | spreading to reflexed | spreading | spreading to reflexed |
| Size of calyx in relation to fruit on secondary fruit | smaller | same size to larger | same size |
| Adherence of calyx | strong | weak to medium | strong |
| Firmness of flesh | firm | soft to medium | firm |
| Evenness of flesh color | slightly uneven | slightly uneven | slightly uneven to even |
| Distribution of flesh color | marginal and central | marginal and central | marginal and central |
| Hollow center size | medium | small | medium |
| Sweetness | medium | medium to strong | medium to strong |
| Texture when tasted | fine to medium | fine to medium | medium |
| Acidity | medium | medium | medium |
| Time of Flowering | late-March | early-March | early-March |
| Harvest Interval in 2002 | late-April thru early-November | mid-April thru early-November | mid-April thru early-November |
| Type of Bearing | partially everbearing | partially everbearing | partially everbearing |

STRESS PEST AND DISEASE RESISTANCE AND SUSCEPTIBILITY

TABLE 3

REACTIONS TO STRESS PESTS AND DISEASES FOR 'DRISCOLL MARIN', 'SAN JUAN' AND 'ANA MARIA'

| | 'MARIN' | 'Ana Maria' | 'San Juan' |
|---|---|---|---|
| Reaction to Stress | | | |
| high pH | moderately resistant | moderately resistant | moderately resistant |
| high soil salt levels | moderately resistant | moderately resistant | moderately resistant |
| Reaction to Pests | | | |
| *Tetranychus urticae* | susceptible | susceptible | moderately susceptible |
| *Lygus hesperus* | susceptible | susceptible | susceptible |
| Reaction To Diseases | | | |
| Botrytis fruit rot | susceptible | susceptible | susceptible |
| Powdery mildew | moderately susceptible | moderately susceptible | susceptible |
| Verticillium wilt | susceptible | susceptible | susceptible |
| Strawberry Mottle Virus | moderately resistant | moderately resistant | moderately resistant |
| *Xanthomanas fragariae* | susceptible | moderately susceptible | moderately susceptible |

ISOZYME ANALYSIS

In addition to the morphological description above, the new cultivar 'Driscoll Marin' has been analyzed to obtain an indication of its genetic makeup to provide further means for identifying the new variety and distinguishing it from some other somewhat similar and/or related strawberry varieties. Specifically, leaf samples of 'Driscoll Marin', 'Ana Maria' and 'San Juan' were analyzed by electrophoresis for isozyme patterns of the enzymes phosphoglucoisomerase (PGI), leucine aminopeptidase (LAP) and phosphoglucomutase (PGM). See *J. Amer. Soc. Hort. Sci.* 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL MARIN', 'ANA MARIA' AND 'SAN JUAN'

| Locus | 'Driscoll Marin' | 'Ana Maria' | 'San Juan' |
|---|---|---|---|
| PGI | A3 | A1 | A2 |
| LAP | B3 | B3 | B3 |
| PGM | C2 | C4 | C4 |

What is claimed is:

1. A new and distinct variety of strawberry plant, substantially as shown and described.

* * * * *